United States Patent [19]

Katagiri et al.

[11] Patent Number: 5,223,419
[45] Date of Patent: Jun. 29, 1993

[54] ALTERATION OF GENE EXPRESSION IN PLANTS

[75] Inventors: Fumiaki Katagiri, New York, N.Y.; Eric Lam, East Brunswick, N.J.; Nam-Hai Chua, Scarsdale, N.Y.

[73] Assignee: The Rockefeller University, New York, N.Y.

[21] Appl. No.: 649,521

[22] Filed: Feb. 1, 1991

Related U.S. Application Data

[63] Continuation-in-part of Ser. No. 323,533, Mar. 14, 1989, Pat. No. 4,990,607.

[51] Int. Cl.$^5$ .................. C12N 15/67; C12N 15/82; C12N 15/29
[52] U.S. Cl. .................. 435/172.3; 435/69.1; 435/70.1; 435/172.1; 435/240.4; 800/205; 935/35; 935/36; 935/67; 536/27
[58] Field of Search .................. 435/172.1, 172.3, 69.1; 935/35, 36

[56] References Cited

U.S. PATENT DOCUMENTS

| | | | |
|---|---|---|---|
| 4,833,080 | 5/1989 | Brent et al. | 435/172.3 |
| 5,023,179 | 6/1991 | Lam et al. | 435/172.3 |

OTHER PUBLICATIONS

Gruissem 1990 (Sep.) The Plant Cell 2:827–828.
Hilson et al 1990 (Jul.) The Plant Cell 1:651–658.
Willmitzer 1988 (Jan.) Trends in Genectics 4:13–18.
Katagiri et al 1989 (Aug.) Nature 340:727–730.
Fromm et al 1989 (Oct.) The Plant Cell 1:977–984.
Sanger et al 1990 Plant Molec Biol 14:433–443.
Fang et al 1989 (Jan.) The Plant Cell 1:141–150.
Ma et al 1988 (Aug.) Nature 334:631–633.
Tabata et al 1989 (Sep.) Science 245:965–967.
Sadowski et al 1988 (Oct.) Nature 335:563–564.
Kadanaga et al 1987 (Dec.) Cell 51:1079–1090.

*Primary Examiner*—Jacqueline Stone
*Assistant Examiner*—P. Rhodes
*Attorney, Agent, or Firm*—Dennis R. Hoerner, Jr.; Howard C. Stanley

[57] ABSTRACT

A transacting DNA binding factor is disclosed. The ASF 1 protein factor specifically binds to the sequence motif TGACG found upstream of the promoter in many plant genes. Coexpression of this protein factor augments the level of expression of the up-regulated promoter containing the TGACG motif.

6 Claims, 9 Drawing Sheets

```
GAATTCTTCAACGTACACCCAATTTGCTGCCTCAAGAAGGATGGGTATATGCGATCCG          58
  N  S  S  T  Y  T  Q  F  A  A  S  R  R  M* G  I  C  D  P          19

ATCCATCAACTTGGCATGTGGGATGATTTCAATAGTAGTTTCCCAAGTACATCGGCAACC       118
 I  H  Q  L  G  M  W  D  D  F  N  S  S  F  P  S  T  S  A  T        39

ATGATTTTAGAAGTTGATAAATGCCTAGAGGACCAGATACCAATTATGGAGAAAAGACTA      178
 M  I  L  E  V  D  K  C  L  E  D  Q  I  P  I  M  E  K  R  L        59

GACAACGAGACAGAAGACACTTCGCATGGAACAGTAGGGACTTCTAACAGATATGAACCG      238
 D  N  E  T  E  D  T  S  H  G  T  V  G  T  S  N  R  Y  E  P        79

GAAACAAGTAAACCCGTCGAGAAGGTACTTAGACGTCTTGCACAAAACCGCGAGGCTGCT      298
 E  T  S  K  P  V  E  K  V  L  R  R  L  A  Q  N  R  E  A  A        99

CGTAAAAGCCGTTTGCGGAAGAAGGCCTATGTTCAGCAGTTAGAAAATAGTAAATTGAAG      358
 R  K  S  R  L  R  K  K  A  Y  V  Q  Q  L  E  N  S  K  L  K       119

CTGATTCAACTGGAACAAGAACTAGAACGCGCCAGAAAACAGGGCATGTGTGTAGGTGGT      418
 L  I  Q  L  E  Q  E  L  E  R  A  R  K  Q  G  M  C  V  G  G       139

GGTGTAGATGCTAGCCAGCTAAGTTACTCTGGAACCGCTAGCTCAGGAACTGCTGTATTT      478
 G  V  D  A  S  Q  L  S  Y  S  G  T  A  S  S  G  T  A  V  F       159

GATATGGAGTATGGTCACTGGGTAGAAGAGCAAACTAGACAAACAAATGACTTAAGGATT      538
 D  M  E  Y  G  H  W  V  E  E  Q  T  R  Q  T  N  D  L  R  I       179

GCTTTGCATTCTCAAATTGGTGAAGCGGAATTGCGCATTATTGTTGATGGTTACCTGAAC      598
 A  L  H  S  Q  I  G  E  A  E  L  R  I  I  V  D  G  Y  L  N       199
```

FIGURE 1A

```
CACTACTTTGATCTCTTCCGCATGAAAGCTACGGCTGCTAAAGCTGATGTCCTATACATC     658
 H  Y  F  D  L  F  R  M  K  A  T  A  A  K  A  D  V  L  Y  I      219

ATGTCTGGTATGTGGAAGACATCTGCCGAGCGCTTTTTCATGTGGATTGGAGGGTTTCGG     718
 M  S  G  M  W  K  T  S  A  E  R  F  F  M  W  I  G  G  F  R      239

CCATCCGAGCTTCTAAAGGTTCTCACACCGCATCTTGAGCTCTTGACAGAACAACAACTT     778
 P  S  E  L  L  K  V  L  T  P  H  L  E  L  L  T  E  Q  Q  L      259

CGAGAGGTTTGTAACCTGACCCAATCATGTCAGCAAGCAGAAGACGCCTTGTCACAAGGA     838
 R  E  V  C  N  L  T  Q  S  C  Q  Q  A  E  D  A  L  S  Q  G      279

ATGGTAAAACTCCACCAGATTCTTGCCGAGGCTGTTGCAGCTGGCCGACTAGGAGAAGGA     898
 M  V  K  L  H  Q  I  L  A  E  A  V  A  A  G  R  L  G  E  G      299

AATTACACTCTTCCGCAGATGGGGCCTGCCATCGAAAAGTTGGAAGATCTTGTTAGGTTC     958
 N  Y  T  L  P  Q  M  G  P  A  I  E  K  L  E  D  L  V  R  F      319

GTAAATCAGGCGGATCATCTACGACAAGAAACCCTCCAACAGATGTCCCGCATCCTTAAT    1018
 V  N  Q  A  D  H  L  R  Q  E  T  L  Q  Q  M  S  R  I  L  N      339

ACGTGCCAAGCAGCTCAGGGCTTACTTGCCTTAGGGGAGTACTTTGAACGACTTCGTGTT    1078
 T  C  Q  A  A  Q  G  L  L  A  L  G  E  Y  F  E  R  L  R  V      359

TTAAGCTCACAATGGGCTACTCGTCTACGTGAGCCTACCTAATGAAGCACAAGAAGATCC    1138
 L  S  S  Q  W  A  T  R  L  R  E  P  T
```

FIGURE 1B

```
GCTGTATATTACTCGAGGAGTTTTGCCTTCAGAAGATGATGCTGTGTTATGGACCAGAGT      1198

ACTGTTGCTCACTTGGTATCTAAACCTATATAATCAGTGGCGGAGCCACACAGGTTCAAG      1258

GGCAGATGCAAATTCAGGATTCCAATGTTATTCGAATCTATTATTTGTACTTATTTACTG     1318

GATTTTAAACACATATATGTGATCTGAGCCAAAAACTACTAGGTTTGGATGAACCCATAA      1378

GTTATACACTAGATCGGCTCCTGCTCAAGGGTGTTCAGTTGAGCATCCTTCGTCGGAAAA     1438

TTATAGTGTGTTATATAAGTCAGATATTATGTGTTGAATCTTGAGCACACTTAGTGTAAT     1498

TCTAGGCTTCGCCATTGAGCTATATTCATTCACTTCAGGTTTGTGGTGAATGAATTTTAC     1558

CATCTTGCTACTTCTGGTAGGGTCTTGAGAACTTAAATGAGATTTTTACACAAATAGCC
```

ALTERATION OF GENE EXPRESSION IN PLANTS

This is a continuation-in-part of our co-pending application Ser. No. 07/323,533 filed Mar. 14, 1989 now U.S. Pat. No. 4,990,607, issued Feb. 5, 1991.

BACKGROUND OF THE INVENTION

The present invention relates to genetic engineering and more particularly to plant genetic engineering. In general, plant genetic engineering involves the introduction of a gene into the genome of a plant to cause expression of a protein in the plant cell or to control the expression of an endogenous plant protein. It is often desirable to be able to readily control the level of expression of a particular gene in plants. Hence, the present invention provides a means to control expression of genes in plants by expressing a transacting DNA binding factor.

It is, therefore, the overall object of the present invention to provide a means to control gene expression in plants.

Accordingly, it is an object of the present invention to provide a means to augment the level of gene expression in all tissues or in specific tissues.

It is yet another object of the present invention to provide a transacting DNA binding factor to control expression of particular plant genes.

These and other objects and advantages of the present invention will be evident to those skilled in the art from the following description.

STATEMENT OF THE INVENTION

In one respect, the present invention provides a transacting DNA binding factor which is useful in the control of plant gene expression. Specifically, a recombinant cDNA clone (hb1) encoding a transacting DNA binding factor which binds to the sequence TGACG has been isolated. The cDNA clone was identified by the ability of its gene product (protein) to bind specifically to a fragment of DNA containing the sequence GGTGACGTG which is found in the upstream region of the wheat histone H3 gene.

Another aspect of the present invention provides a method for altering the expression of a plant gene having a promoter comprising an upstream sequence TGACG by inserting into the genome of the plant cell a chimeric gene which functions in plants and codes for the ASF-1 protein.

Cloning of the hb1 DNA Binding Factor

Various promoters of genes, not only in plant but also in animal, contain a TGACG motif in their upstream regions. Our study showed that the region which includes the direct repeat of TGACG motifs in CaMV35S promoter (as-1 sequence) has a very important role in the expression of 35S promoter in two ways: its expression in root and then conferring the effect of distal enhancers on the promoter. An as-1 sequence specific DNA binding factor (ASF-1) was characterized in vitro in pea and tobacco extracts. The in vitro study also showed that TGACG motifs in nopaline synthase gene promoter of Ti-plasmid (nos1 sequence) and histone H3 gene promoter of wheat (hex1 sequence) were recognized by similar binding factors.

For the further characterization of the DNA binding factors, the direct cloning of the genes for the factors was performed by means of screening an expression library with a radioactively labelled DNA binding site. An expression cDNA library was constructed in lambda gt11 vector with random-primed cDNA derived from polyA+ RNA of dark-adapted tobacco leaves. There were three reasons why the library was made from dark-adapted tobacco leaf RNA; because all of our in vivo study on cis-regulatory regions had been done in transgenic tobacco, genes for the factors are preferably isolated from the homologous system; the binding activity to as-1 sequence was observed to be much higher in the extract of dark-adapted tobacco leaves than in light-grown ones; the relative ratio of a certain mRNA species to total mRNA is higher in dark-adapted leaves because mRNA synthesis for photosynthetic machinery is shut down. As the specific DNA sequence probe, a concatemerized hex1 sequence (CGCGGATTGGT GACGTGGCCG) was used because the structure of the TGACG containing region seemed more simple than those of the other binding sites. Five positive clones were obtained out of 60,000 recombinants after the primary screening. These clones were named lambda hb1, 2, 3, 5, and 6. Rescreening the filters with the wild-type probe (hex1) and a mutant probe (CGCGGATTTATGGCCG) in parallel demonstrated that only the wild-type probe bound to the proteins encoded by these recombinant phages. Lysogen extract made from lambda hb1 showed specific binding not only to hex1 sequence but also to as-1 sequence, nos1 sequence, and an upstream sequence of octopine synthase gene of Ti-plasmid, which has two TTACG motifs in it. A brief restriction mapping revealed that the sizes of the inserts in lambda hb1, 2, 5, and 6 are 1.2 kb, 0.5 kb, 1.2 kb, 1.6 kb, and 1.7 kb, respectively.

Figure 1A:
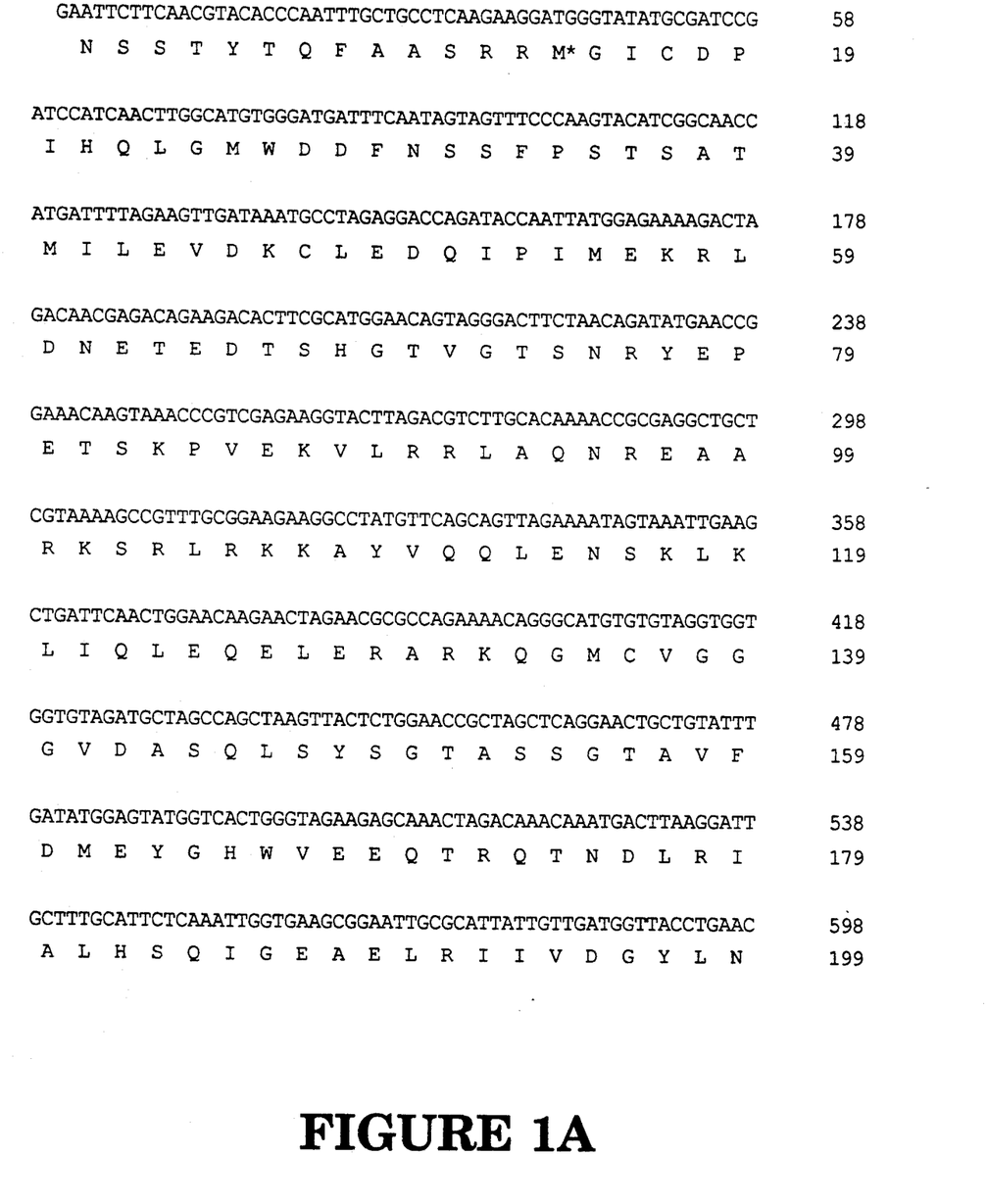
FIGS. 1A, 1B, and 1C represent the DNA sequence (and its deduced amino acid sequence) for clone hb1 which encodes a trans-acting DNA binding factor (ASF-1).
Figure 1B:
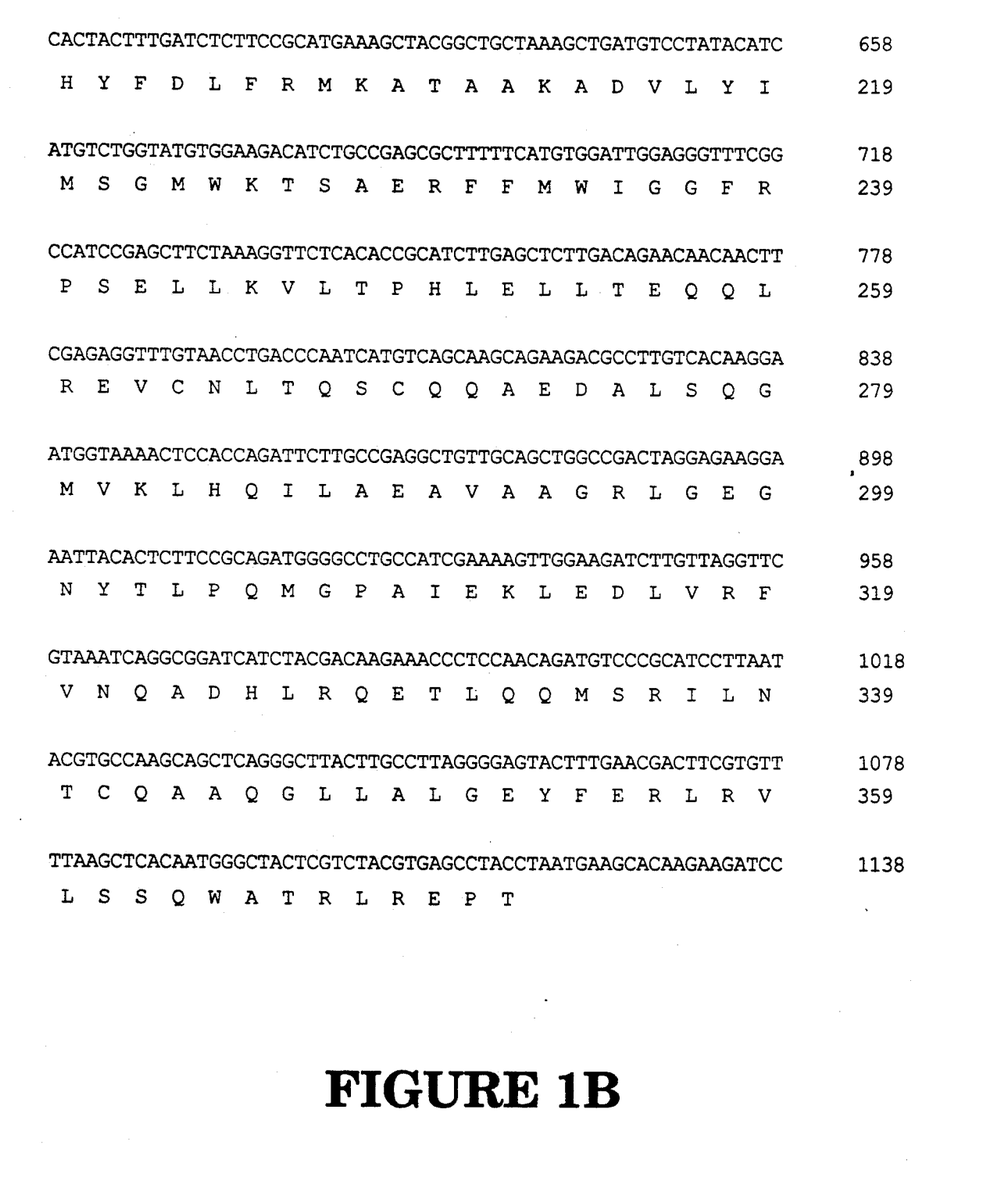
Figure 1C:
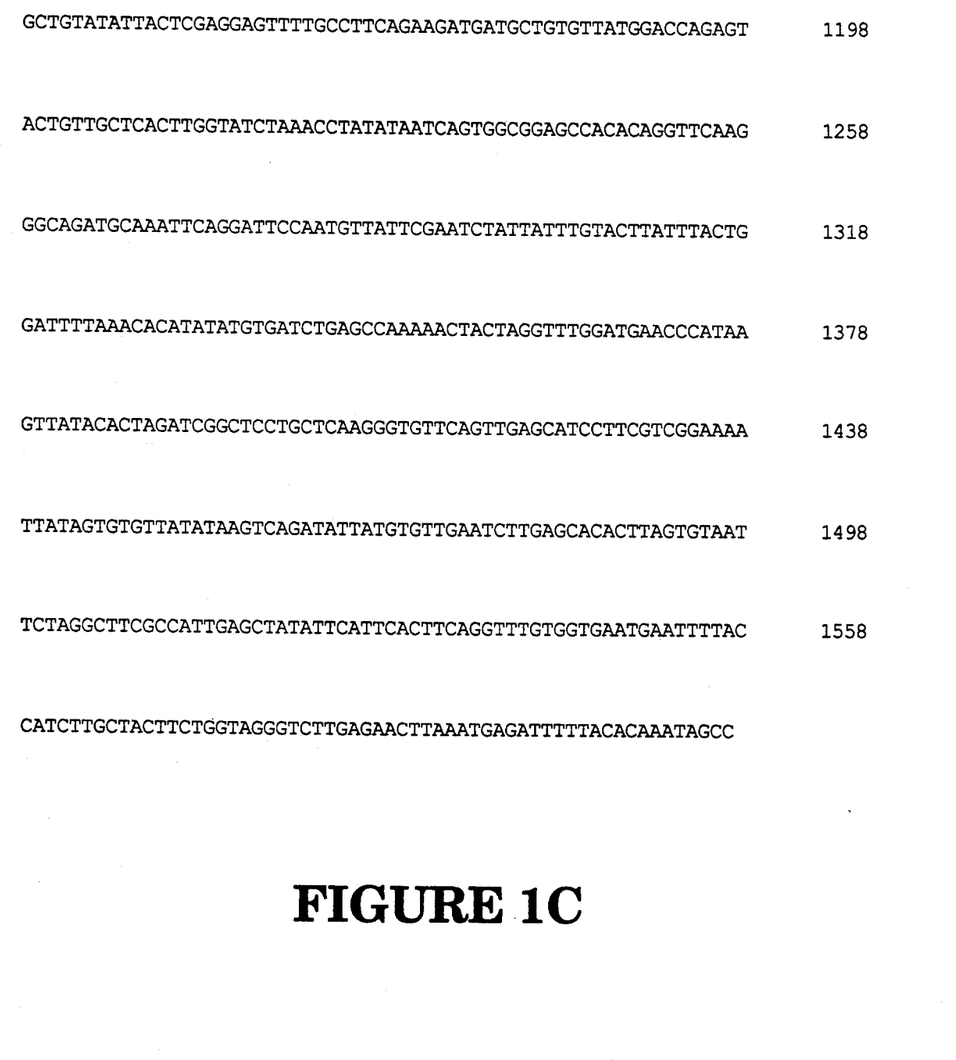

FIGS. 1A, 1B, and 1C show the nucleotide sequence (and deduced amino acid sequence) of the insert of clone hb1. The protein product (transacting DNA binding factor) bound specifically to a DNA fragment containing the sequence GGTGACGTG from the wheat histone H3 gene as well as DNA fragments found upstream of the cauliflower mosaic virus 35S gene and the nopaline synthase gene of the Ti plasmid of *Agrobacterium tumefaciens.*

Alteration of Gene Expression in Plants

While not fully understood, the data suggest that the transacting DNA binding factor (ASF-1) is able to bind to specific DNA sequences and is able to activate transcription from promoters that contain the specific DNA sequences. Factor ASF-1 recognizes the sequence motif TGACG which is found in plant genes such as histone genes (Mikami et al., 1987); enzyme genes for agropine biosynthesis (Velten et al., 1984); the octopine synthase gene (Ellis et al., 1987); and the mannopine synthase gene (DeRita and Gelvin, 1987); as well as the CaMV35S gene, the full-length transcript gene from Figwort Mosaic Virus, histone H3 gene and nopaline synthase gene.

The recombinant cDNA clone encoding a transacting DNA binding factor able to bind specifically to sequences found upstream of the CaMV35S gene and upstream of cellular genes and able to activate transcription from these promoters can be used for many purposes. These purposes include but are not limited to the following:

1. Augmenting the levels of expression in all tissues or in specific tissues and under specific environmental conditions of cellular genes the promoters of which contain the binding site. This can be accomplished by causing expression of the ASF-1 protein encoded by the recombinant cDNA clone to be regulated by a promoter that confers expression in particular tissues or is responsive to particular environmental stimuli. Examples of such promoters include but are not limited to the promoters from the genes for (i) the small subunit of ribulose bisphosphate carboxylase (rbcS) which is expressed primarily in tissue that contains chloroplasts and is responsive to light (Aoyagi et al., 1988), (ii) the chlorophyll A/B binding protein which is expressed in immature leaves, is responsive to light and is regulated by an internal circadian clock (Nagy et al., 1988), (iii) the heat-shock proteins, which are inducible by increases in ambient temperature (Strittmatter and Chua, 1987), (iv) the nopaline synthase promoter from *Agrobacterium tumefaciens* which is expressed in all tissues but is expressed preferentially in mature leaves and roots (An et al., 1986). The promoters from these genes would be placed upstream of the DNA fragment encoding the ASF-1 protein and the recombinant chimeric construct would be introduced into plants using standard techniques for generating transgenic plants.

2. Changing the levels of expression of cellular genes that contain the binding site by changing the structure of the protein encoded by the recombinant cDNA clone is another utility. It has been shown that transacting factors are frequently made up of at least two functional domains, one domain is responsible for binding DNA, the second domain is responsible for activating transcription (Ptashne, 1988). From comparison of the amino acid sequence of the ASF-1 protein with other trans-acting DNA binding proteins it appears likely that the ASF-1 protein contains these two types of domains. Modifications of the ASF-1 protein in order to change the levels of expression of cellular genes to which it binds can include but are not limited to the following:

a) The activation domain can be replaced by an activation domain from another trans-acting factor. It has been shown that replacement of the activation domain of a yeast transacting factor, Gal-4, with the activation domain of a transacting factor from herpes simplex virus, VP16, results in a hybrid trans-acting factor with greatly increased activating potential (Sadowski et al., 1988). Replacement of the activating domain of ASF-1 with the activating domain of VP16 should result in increased activating potential of ASF-1. Replacement of the activating domain of ASF-1 with DNA fragments that encode putative activating domains, for example the highly acidic region of CaMV open reading frame IV (21 acidic residues and two basic residues out of 51 amino acid residues, Henle et al., 1982) could result in increased activating potential of ASF-1. In addition this would be a way of testing whether a putative activating domain could indeed function as an activating domain. Replacement of the activating domain of ASF-1 with the activating domain of the heat shock activating factor HSTF or HSF (Wiederrecht et al., 1988; Sorger and Pelham, 1988) could result in heat inducible expression of cellular genes that contain the binding site for ASF-1. Recombinant constructs containing the DNA encoding the chimeric proteins would be made and then fused to certain promoters including but not limited to the promoters listed above in section 1 and introduced into plants using standard techniques for generating transgenic plants.

b) Expression of the DNA binding domain without an activation domain can result in inhibition of expression from genes which contain the binding site in the promoter (Friedman et al., 1988). Expression of the DNA binding domain of ASF-1 without an activation domain could result in inhibition of expression of genes that contain the binding site in the promoter. The cauliflower mosaic virus contains a binding site for ASF-1 upstream of the 35S gene promoter. The DNA fragment from the recombinant cDNA that encodes the DNA binding domain of ASF-1 would be fused to certain promoters including but not limited to the promoters listed in section 1 and introduced into plants using standard techniques for generating transgenic plants.

c) Expression of RNA that is complementary to the RNA that encodes a protein can result in inhibition of expression of the protein. The complementary RNA is termed "antisense RNA" (Green et al., 1986). Expression of antisense RNA complementary to the RNA encoding ASF-1 could result in a decreased concentration of the ASF-1 protein. If expression of a viral gene that contains the binding site for ASF-1 in its promoter is dependent upon a certain concentration of ASF-1 protein, expression of antisense RNA complementary to the ASF-1 RNA may cause inhibition of viral replication. The DNA fragment from the recombinant cDNA that encodes ASF-1 would be placed in an orientation so that RNA complementary to the RNA encoding ASF-1 would be produced and fused to certain promoters including but not limited to the promoters listed in section 1 and introduced into plants using standard techniques for generating transgenic plants.

Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA, and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of Agrobacterium tumefaciens). The cauliflower mosaic virus (CaMV) 19S and 35S promoters (Odell et al., 1985), the full-length transcript promoter from Figwort Mosaic Virus (FMV) (Gowda et al. 1989), the light-inducible promoter from the small subunit of ribulose bis-phosphate carboxylase (ssRUSICSO, a very abundant plant polypeptide), and the mannopine synthase promoter (Velten et al., 1984, and Velten & Schell, 1985). All of these promoters have been used to create various types of DNA constructs which have been expressed in plants, see e.g. PCT publication WO84/02913 (Rogers et al., Monsanto). Promoters which are known or are found to cause transcription of RNA in plant cells can be used in the present invention. Such promoters may be obtained from plants or viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of the ASF-1 protein to cause enhancement of the desired gene expression. The amount of ASF-1 protein needed may vary with the target promoter to be affected and the cell type or plant species. Accordingly, while the CaMV35S promoter is often preferred, it should be understood that this promoter may not be the optimal one for all embodiments of the present invention, particularly where selective expression of the ASF-1 protein is desired. The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. Alternately, the strength of a promoter may be increased by inserting additional copies of enhancer elements as described by Kay et al., 1987. The resulting chimeric promoter may be used as described herein. For purposes of this description, the phrase "CaMV35S" promoter thus includes variations of CaMV35S promoter, e.g., promoters derived by means of ligation with different regulatory regions, random or controlled mutagenesis, addition of multiple enhancer elements, etc. A promoter that is also particularly useful in the present invention is the FMV promoter.

The DNA constructs of the present invention contain, in double-stranded DNA form, a structural gene sequence which encodes the ASF-1 protein. A coding sequence used in a DNA construct of this invention may be modified, if desired, to create mutants, either by random or controlled mutagenesis, using methods known to those skilled in the art. Such mutants and variants are therefore within the scope of the present invention. Accordingly, the phrase "ASF-1 protein" is used here to include truncated proteins and fusion proteins, as well as unmodified ASF-1 protein.

The 3' non-translated region contains a polyadenylation signal which functions in plants to cause the addition of polyadenylate nucleotides to the 3' end of the mRNA. Examples of suitable 3' regions are (1) the 3' transcribed, non-translated regions containing the polyadenylated signal of genes from the T-DNA of Agrobacterium, the soybean storage protein genes and the small subunit of the RuBP carboxylase gene.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The non-translated leader sequence can be part of the promoter sequence, or can be derived from an unrelated promoter or coding sequence as discussed above.

Plant Transformation/Regeneration

A DNA construct of the present invention can be inserted into the genome of a plant by any suitable method. Suitable plant transformation vectors include those derived from a Ti plasmid of *Agrobacterium tumefaciens*, such as those described by Herrera-Estrella (1983), Bevan (1983), Klee (1985), Fraley (1985) and EPO publication 120,516 (Schilperoort, et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, transformation using viruses or pollen and the use of microprojectiles.

Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers) and various floral crops. Gene expression can be altered in plants from each of the aforesaid families pursuant to the present invention.

In the examples that follow, tobacco plants are transformed generally by the method of Horsch et al. (1985). In particular, tobacco (*Nicotiani tabacum var. samsun*) leaf disks with diameters of about 6 mm are taken from surface sterilized tobacco leaves. These disks are cultivated on MS104 agar medium for two days to promote partial cell wall formation at the wound surfaces. The leaf disks are then submerged in a culture of *A. tumefaciens* cells containing the chimeric gene of interest and plasmid pMP90RK which has been grown overnight in Luria broth at 28° C., and shaken gently. The leaf disks are removed from the bacterial suspension, blotted dry, and incubated upside down on filter paper placed over "nurse" cultures of tobacco cells as described by Horsch et al. (1980). After two or three days, the disks are transferred to petri dishes containing MS media with 500 µg/ml carbenicillin with no nurse culture.

Within ten days after transfer to the MS media, actively growing callus tissue appears on the periphery of all disks on the transformed plates. Transformed tobacco plants are produced by regeneration from the above-described transformed leaf disks according to the procedure described in Horsch et al. (1985). Resistance to methotrexate is used as the selection criterion and performed as described in Eichholtz et al. (1987).

EXAMPLE 1

To test the effect of the ASF-1 protein on the expression of the full-length transcript promoter from Figwort Mosaic Virus (FMV), plant tissue expressing the β-glucuronidase gene (GUS) was transformed with a vector carrying the gene encoding ASF-1 (denoted TGA1a in the accompanying Figures).

In particular, the pMON994 vector was mobilized into *A. tumefaciens* strain ABI using the triparental conjugation system (Ditta et al. 1980). Tobacco leaf disks were transformed by the *A. tumefaciens* cells containing pMON994 and transgenic plants produced by the regeneration of the transformed callus tissue, as described above.

Figure 2:
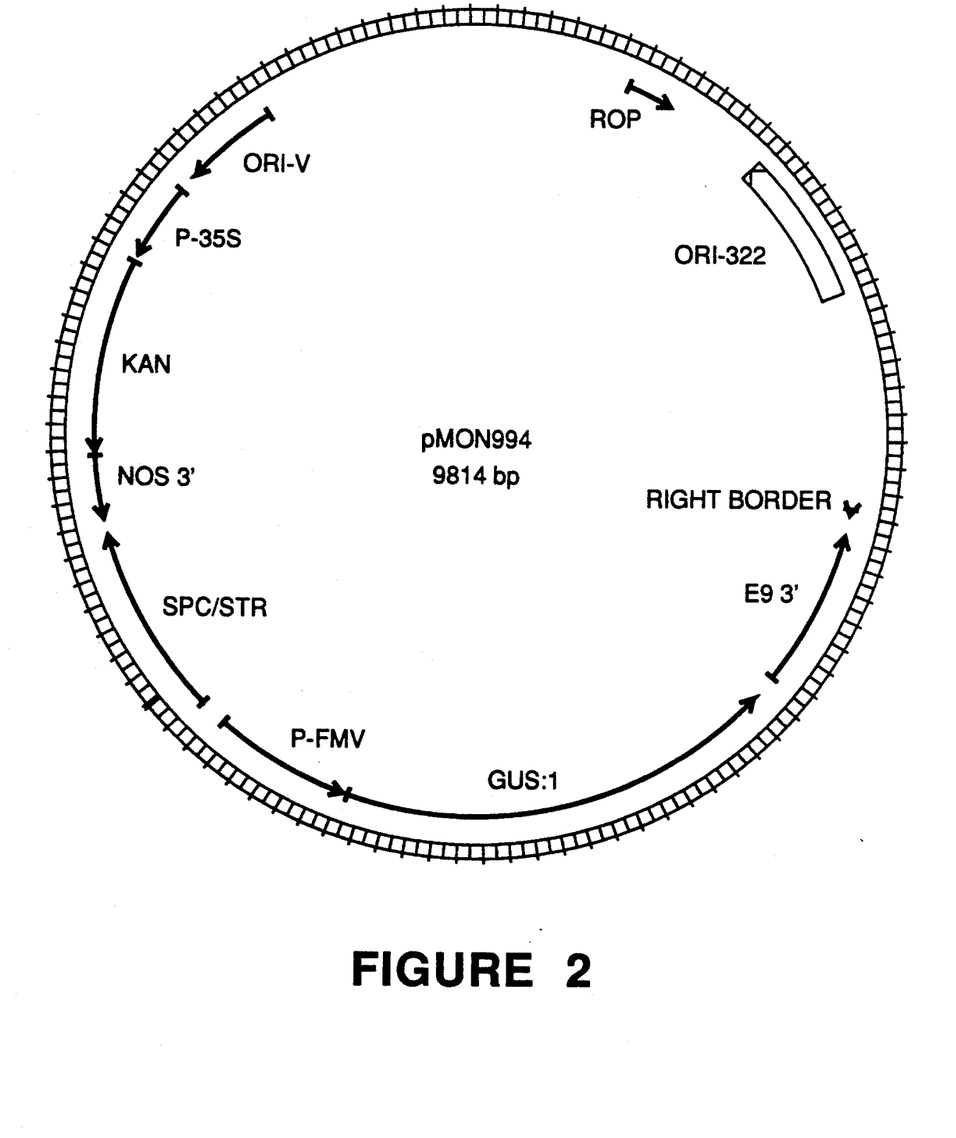
FIG. 2 is a physical map of pMON994.

As shown in FIG. 2, pMON994 has the following elements; a 0.93 kb fragment isolated from transposon Tn7 encoding a bacterial spectinomycin/streptomycin resistance gene (Spc/Str) that functions as a marker for selection of the plasmid in *E. coli* and Agrobacterium (Fling, M. E., et al. 1985); a 1.61 kb segment of DNA encoding a chimeric kanamycin resistance gene (P-35S/Kan/NOS3') that permits selection of transformed plant cells (Beck, E., et al. 1982); a 0.75 kb oriV DNA sequence containing the origin of replication from the Rk2 plasmid (Stalker, D. M., et al. 1979); a 3.1 kb segment of pBR322 (ori-322) that provides the origin of replication for maintenance in *E. coli* and the bom site for the conjugational transformation to the Agrobacterium cells (Sutliffe, J., 1979); a 0.36 kb segment from pTiT37 (the PvuI to BclI fragment) that carries the nopaline-type T-DNA right border (Fraley et al. 1985); and a 1.15 kb expression cassette consisting of the 0.6 kb FMV full-length transcript promoter (Gowda et al. 1989), several unique restriction sites, and the 0.7 kb 3' non-translated region of the pea ribulose bisphosphate carboxylase small subunit E9 gene (E9 3') (Coruzzi, G., et al., 1984 and Morelli, G. et al., 1985). The *E. coli* β-glucuronidase coding sequence is inserted into the unique BglII site in the FMV-E9 3' cassette. The resulting plasmid contains the GUS gene under control of the FMV promoter.

Figure 3:
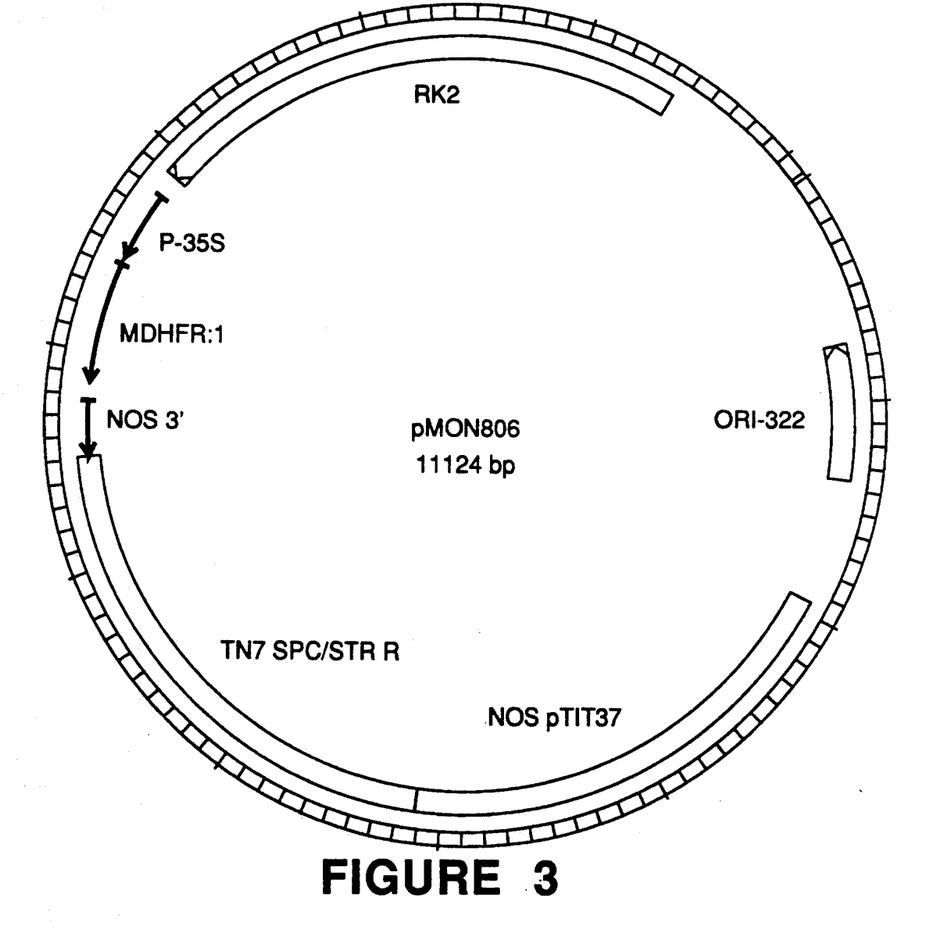
FIG. 3 is a physical map of pMON806.
Figure 4:
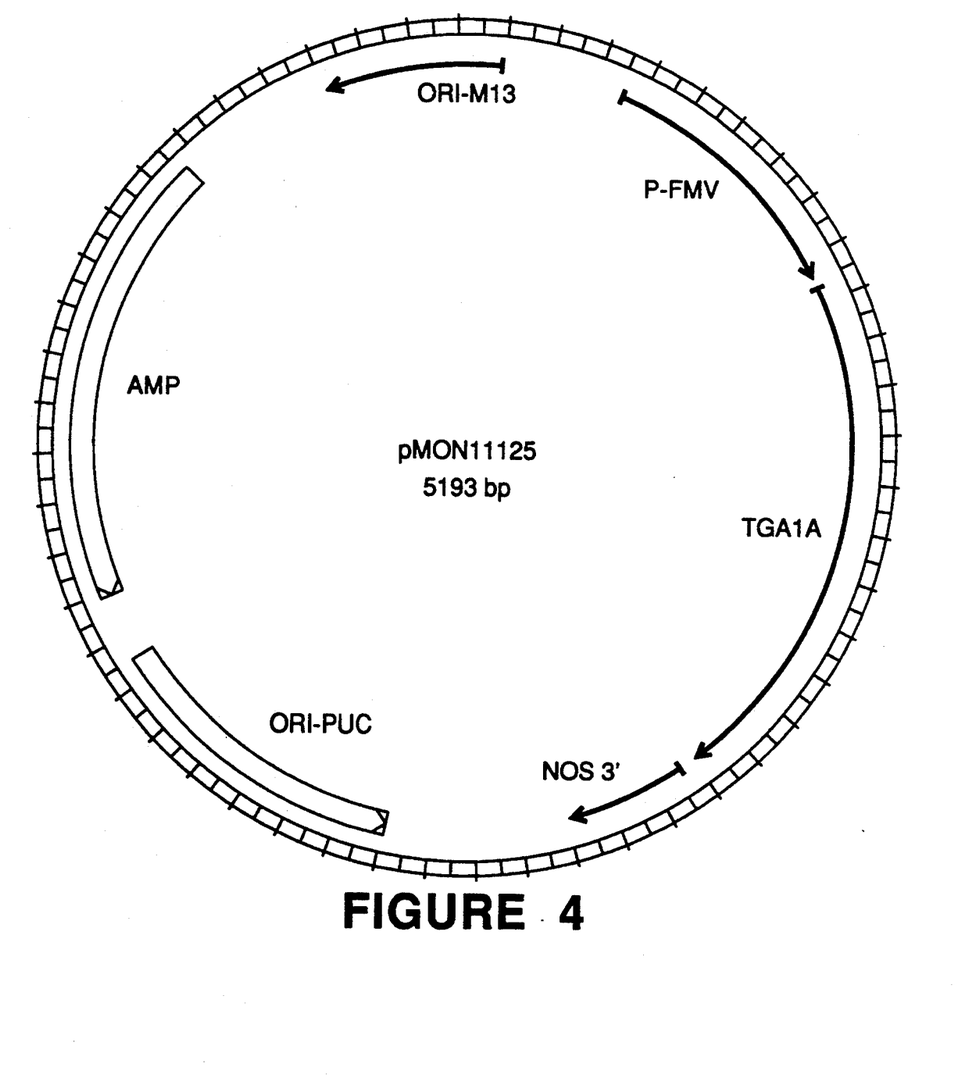
FIG. 4 is a physical map of pMON11125.
Figure 5:
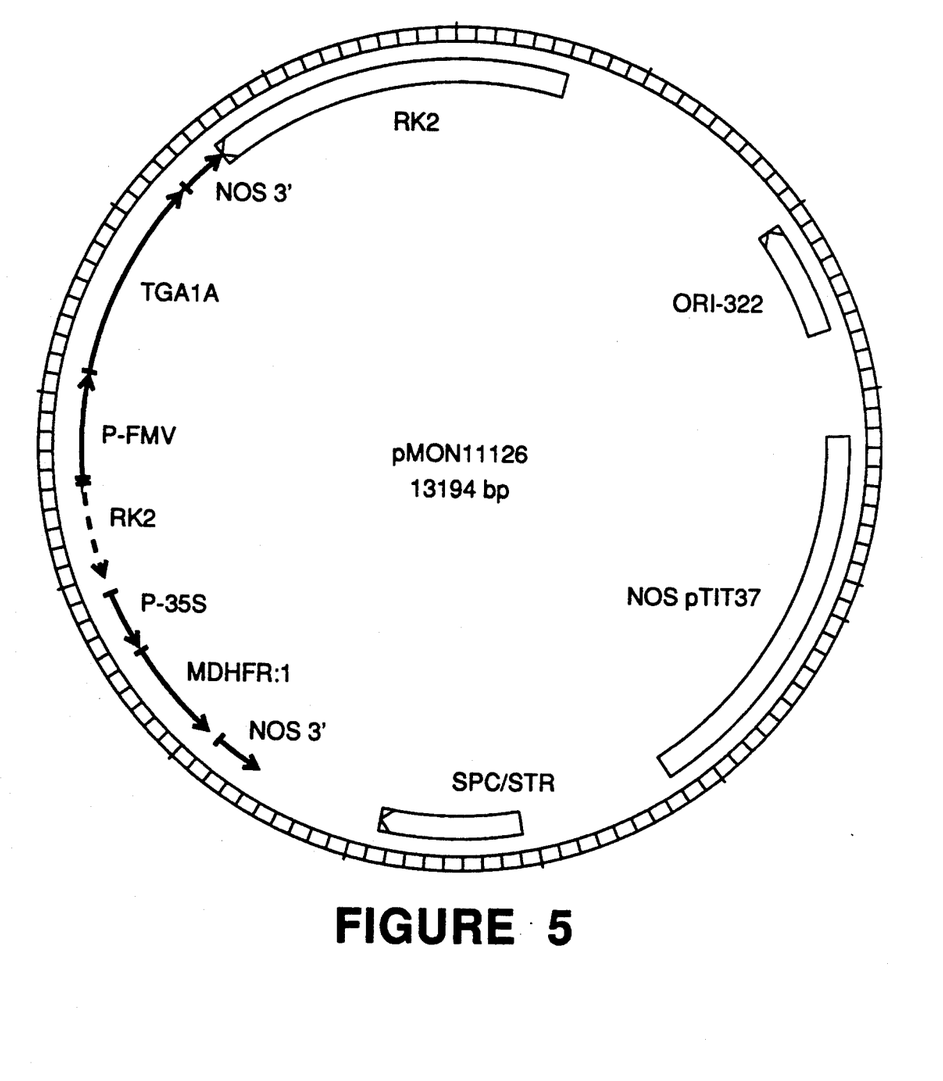
FIG. 5 is a physical map of pMON11126.
Figure 6:
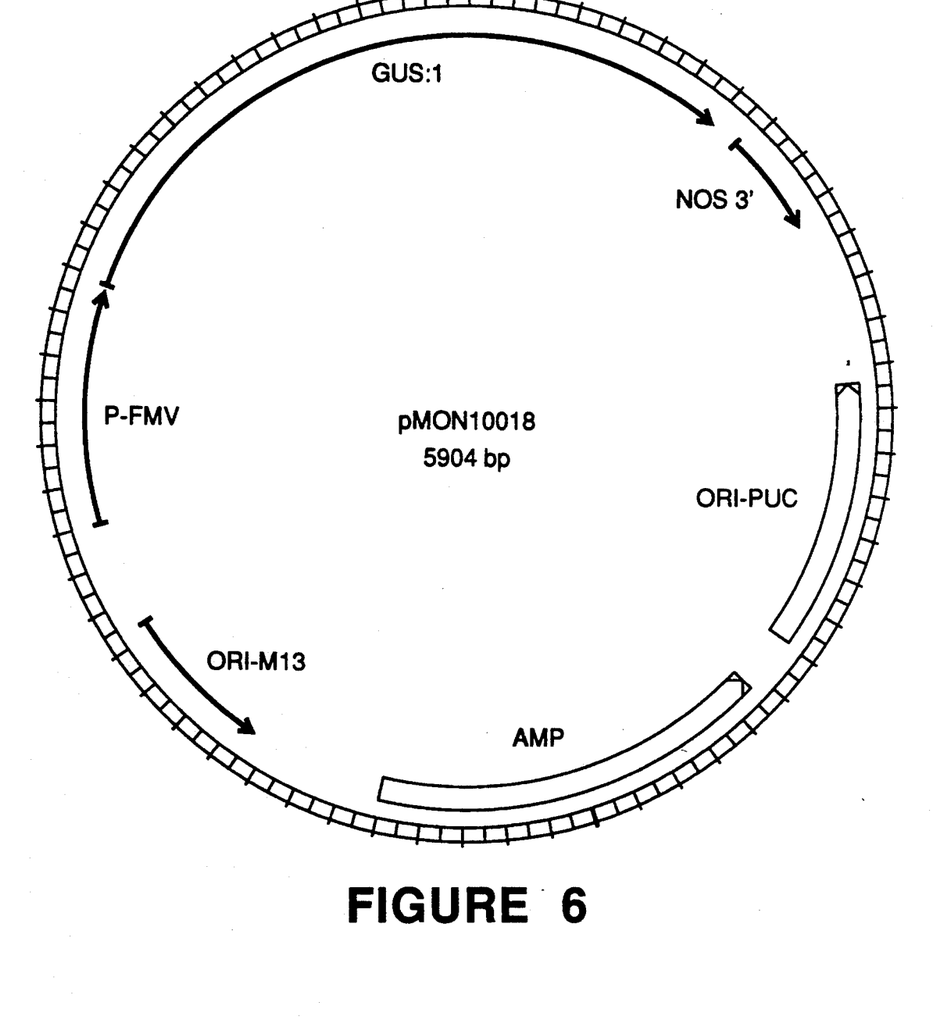
FIG. 6 is a physical map of pMON10018.

Transgenic plants containing pMON994 were assayed for GUS activity using the X-gluc staining assay as described by Jefferson et al. (1987). Tissue expressing the GUS gene stains blue in the presence of X-gluc. $R_1$ plants expressing the GUS gene and also expressing the KAN gene (which encodes the enzyme NPTII and permits selection of transformed plants by their resistance to the antibiotic kanamycin) were selected for further transformation. Plasmid pMON11126 was mobilized into *A. tumefaciens* strain ABI using the triparental conjugation system (Ditta et al. 1980). pMON11126 was constructed by inserting a 1.457 kb CaMV 35S/dhfr/NOS fragment from pMON809 as described in Eichholtz et al. (1987) into pMON505 (Horsch and Klee 1986). This fragment replaces the NOS-NPTII-NOS region to create pMON806 as shown in FIG. 3. The 2.07 kb FMV-TGAla-NOS3' containing fragment from pMON11125 (FIG. 4) was inserted into pMON806 to create pMON11126 as shown in FIG. 5. pMON11125 was created by inserting the 1.177 kb ASF1 cDNA (Katagiri et al. 1989) into pMON10018 which replaces the GUS coding sequence. pMON11125 is shown in FIG. 4. pMON10018 was created by inserting the 0.6 kb full-length transcript promoter from the Figwart Mosaic Virus (Gowda et al 1989) fused to the 1.9 kb coding sequence for β-glucuronidase (GUS) (Jefferson et al. 1987) and fused to the 0.3 kb 3' nontranslated region of the nopaline synthase gene (NOS 3') (Fraley et al. 1983) into a derivative of pUC119 (Vieira and Messing 1987). pMON10018 is shown in FIG. 6. *A. tumefaciens* cells containing pMON11126 were then transformed into tobacco leaf disks as previously described and as modified for methotrexate selection by Eichholtz et al. (1987).

The transgenic methotrexate resistant plants obtained as described above were analyzed for GUS expression by the method of Jefferson et al. (1987) with the following modifications. A 1 gram $10^{th}$ internode leaf was excised and prepared for assay by freezing in liquid nitrogen, grinding with mortar and pestle, and adding 2 mls 0.1M $KPO_4$, pH7.8, 1 mM EDTA, 10 mM DTT, 0.8 mM PMSF, and 5% glycerol (extraction buffer). The fluorogenic reaction was carried out in 2 mM 4-Methylumbelliferyl-β-D-Glucuronide (MUG). Fluorescence was measured using a Hoescht DNA Fluorometer (Model TKO 100). Protein concentrations of plant extracts were determined by optical density [protein concentration (mg/ml)=$1.5 \times OD_{280} - 0.75 \times OD_{260}$].

Results of the GUS expression assays on five different transgenic tobacco plants and a control plant which was transformed only with pMON994 are shown in Table 1. Relative expression (RE) was determined by setting the control plant, #14515, to 1 and dividing its specific activity (pmol/min/mg of protein) into the specific activity of the transgenic plants expressing ASF-1

TABLE 1

| Plant # | Specific activity (pmol/min/mg) | RE |
|---------|-------------------------------|-----|
| 14515   | 31,000                        | 1.0 |
| 31179   | 39,605                        | 1.3 |
| 31180   | 81,513                        | 2.6 |
| 31184   | 85,782                        | 2.7 |
| 31182   | 120,751                       | 3.9 |
| 31177   | 209,156                       | 6.7 |

These results demonstrate an increased expression of the GUS gene when the ASF-1 cDNA is introduced into a plant already expressing the GUS gene under the control of a heterologous promoter.

EXAMPLE 2

To test the effect of the ASF-1 protein on the expression of the enhanced CaMV35S promoter (e35S) as described in Kay et al. (1987), plant tissue expressing the β-glucuronidase gene (GUS) was transformed with a vector carrying the gene encoding ASF-1.

Figure 7:
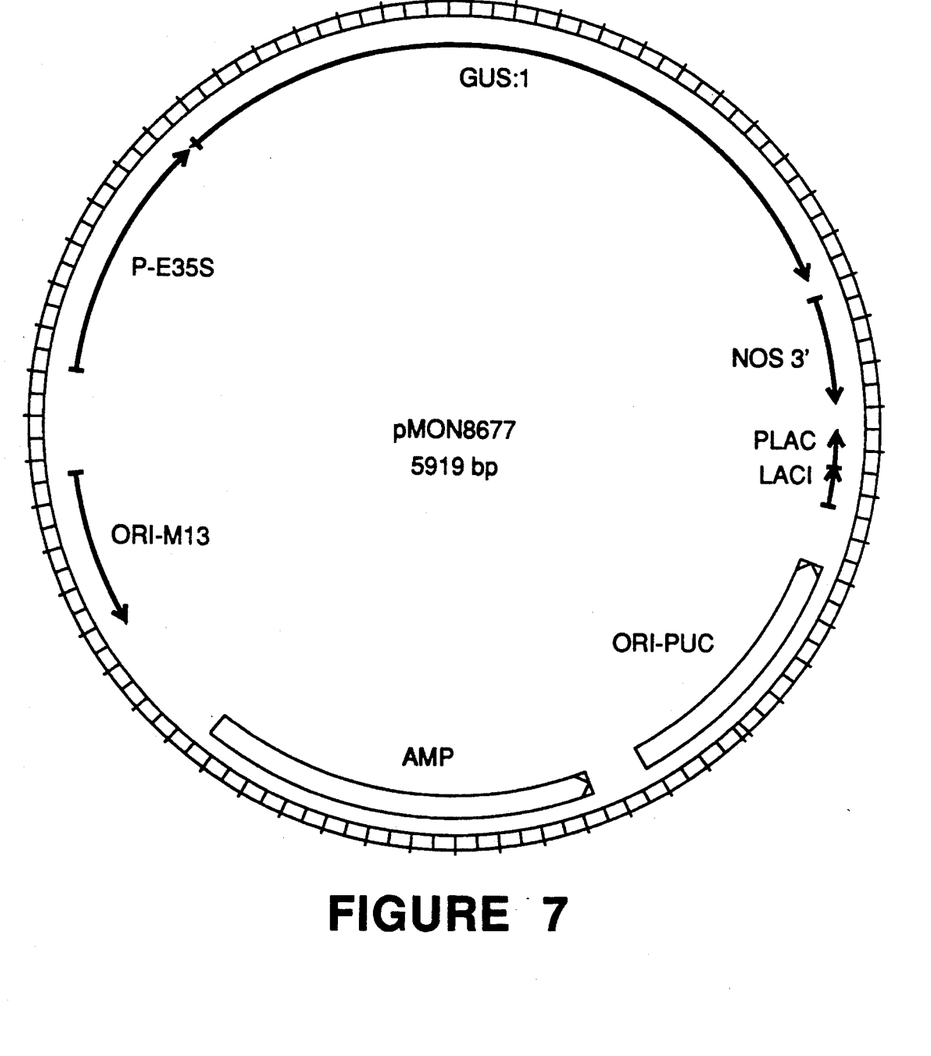
FIG. 7 is a physical map of pMON8677.

The pMON8677 vector alone or with the pMON11126 vector were electroporated into tobacco Txd (Tobacco xanthii diploid) cells. pMON8677 was created by inserting the 0.655 kb enhanced CaMV 35S promoter (Kay et al 1987) fused to the 1.9 kb coding sequence for β-glucuronidase (GUS) (Jefferson et al. 1987) and fused to the 0.3 kb 3' nontranslated region of the nopaline synthase gene (NOS 3') (Fraley et al. 1983) into a derivative of pUC119 (Vieira and Messing 1987). pMON8677 is shown in FIG. 7 and was used as a control. pMON11126 is as described in Example 1.

Tobacco Txd cells were grown in 250 ml flasks at 25° C. and 138 rpm in the dark (covered with aluminum foil). A sub-culture volume of 9 ml was removed and added to 40 ml fresh Txd media every 3–4 days, once the cell line was established and actively growing. Txd media contains MS salts, 3% sucrose, 0.2 g/l inositol, 0.13 g/l asparagine, 80 μl of 50 mg/ml stock of PCPA, 5 μl of 1 mg/ml stock of kinetin and 1 ml of 1000× vitamins (1.3 g/l nicotinic acid, 0.25 g/l thiamine, 0.25 g/l pyridoxine HCL, and 0.25 g/l calcium pantothenate), pH 5.8. Four flasks of Txd media (40 mls) were inoculated with 16 ml of a 2 day old suspension culture. After approximately 24 hours, cells were spun down in 50 ml sterile centrifuge tubes (one flask/tube) at 800–1000 rpm (200 xg) for 5 minutes. The supernatant was removed and saved as conditioning media. Forty (40) ml of enzyme mix containing protoplast isolation media (PIM), 0.5% BSA (Sigma A-3350), 40 μl mercaptoethanol, 0.5% cellulase 'RS', 0.5% rhozyme, and 0.02% Y-23 pectolyase was added to each tube, mixed with a wide bore or broken tip pipette and pipetted into 100×25 mm petri dishes (10 ml/plate). PIM contains 7.35 g/l calcium chloride, 1 g/l sodium acetate, and 45 g/l mannitol (pH 5.8). The petri dishes were covered with parafilm and incubated at 26°-28° C. on a rotary shaker at 50-60 rpm for one hour in the light. Digestion was monitored by observation through an inverted microscope. The protoplasts were pipeted back into 50 ml sterile centrifuge tubes using 10 ml pipettes with standard tips. The protoplasts were spun down at 800-1000 rpm for 5 minutes. The supernatant discarded and the protoplasts gently resuspended in 20 ml PIM. This was repeated and the protoplasts resuspended in 20 ml of electroporation buffer (EB). EB contains 0.02 g/l $KH_2PO_4$, 0.115 g/l $Na_2HPO_4$, 7.5 g/l NaCl, and 36.4 g/l Mannitol (pH 7.2). The protoplasts were counted using a hemacytometer and yields determined. The protoplasts were spun down again and resuspended in EB to a protoplast density of $4 \times 10^6$ cells per ml and held on ice. 0.4 ml of protoplasts in EB were added to a 0.8 ml cuvette with 0.4 ml EB containing the above described DNA. The protoplasts and DNA were mixed by gently inverting the cuvette twice and electroporated at 150 volts and a capacitance of 500 $\mu$Farads. The mixture was incubated on ice for 10 minutes and then warmed to room temperature for 10 minutes. The resulting protoplasts were resuspended in 7 ml of Txd+0.4M Mannitol (that has been diluted to total volume and 1x concentration with the saved "conditioning media") in 100×25 mm petri dishes. The electroporated protoplasts are grown in the light at 26°-28° C. and harvested in 20-24 hours to assay for transient GUS activity.

The electroporated cells obtained, as described above, were analyzed for GUS expression by the method of Jefferson et al. (1987) with the following modifications. Cells were lysed for assay by freeze/thawing in liquid nitrogen and 2 mls 0.1M $KPO_4$, pH7.8, 1 mM EDTA, 10 mM DTT, 0.8 mM PMSF, 5% glycerol (extraction buffer). The fluorogenic reaction was carried out in 2 mM MUG. Fluorescence was measured using a Hoescht DNA Fluorometer (Model TKO 100).

Results of the GUS expression are shown in Table 2. These calculations are based upon triplicate sampling. The resulting slope of MU(4-methylumbelliferyl) fluorescence versus time is compared for relative expression as described in Jefferson et al. (1987).

TABLE 2

| Construct | slope MU | Average MU | RE |
| --- | --- | --- | --- |
| pMON8677 | | | |
| A | 11.0 | | |
| B | 5.9 | 8.4 | 1 |
| C | 8.4 | | |
| pMON8677 + pMON11126 | | | |
| A | 22.1 | | |
| B | 16.3 | 17.8 | 2.1 |
| C | 15.0 | | |

These results demonstrate an increased expression of the GUS gene driven by the enhanced CaMV35S promoter by the introduction of the cDNA of ASF-1 into plant cells.

BIBLIOGRAPHY

An, et al. (1986) *Mol. Gen. Genet.* 203:245.
Aoyagi, et al. (1988) *Mol. Gen. Genet.* 213:179.
Bevan, M. et al. (1983) *Nature* 304:184.
DiRita and Gelvin (1987) *Mol. Gen. Genet.* 207:233.
Ditta, G., et al., *Proc. Natl. Acad. Sci. USA*, 77:7347-7351 (1980).
Eichholtz, D. A., et al., *Somatic Cell and Mol. Gen.*, 13:67-76 (1987).
Ellis, et al. (1987) *EMBO J.* 6:3203.
Fraley, R. T. and Rogers, S. et al. (1985) *Biotechnology* 3:629.
Fraley, R. T., et al., *Proc. Natl. Acad. Sci. USA*, 80:4803-4807 (1983).
Friedman et al. (1988) *Nature* 335:452.
Gowda, S., Wu, F. C. and Shepard, R. J., *J. Cellular Biochem*, 13D, 301 (1989).
Green, et al. (1986) *Ann. Rev. Biochem*, 55:569.
Henle, et al. (1982) *Current Topics in Microbiol, and Immunol*, 96:193.
Herrera-Estrella, L. et al. (1983) *Nature* 303:209.
Horsch, R., Fry, J., Hoffman, N., Wallworth, M., Eichholtz, D., Rogers, S. and Frayley, R., *Science*, 227:1229-1231 (1985).
Horsch, R. and Jones, G., *In Vitro*, 16:103-108 (1980).
Horsch, R. and Klee, H., *Proc. Natl. Acad. Sci. USA*, 83:4428-4432 (1986).
Jefferson, R. A., Kavanagh, T. A. and Bevan, M. W., *EMBO J.*, 6:3901-3907 (1987).
Katagiri, F., Lam, E. and Chua, N.-H., *Nature*, 340:727-730 (1989). Kay, R. et al. (1987) ScienceI 236:1299-1302.
Klee, H. J. et al. (1985) *Bio/Technology* 3:637-642.
Kozak, M. (1984) *Nature* 308:241-246.
Mikami, et al. (1987) *FEBS Lett.* 223:273.
Nagy, et al. (1988) *Genes & Develop.* 2:376.
Odell, J. T., Nagy, F., Chua, N. H., (1985) *Nature* 313:810.
Ptashne (1988) *Nature* 335:683.
Sadowski, et al. (1988) *Nature* 335:563.
Sorger and Pelham (1988) *Cell* 54:841.
Strittmatter and Chua (1987) *Pro. Natl. Acad. Sci.* 84:8976.
Velten, et al. (1984) *EMBO J.* 3:2723-30.
Velten and Schell (1985) *Nucleic Acid Res.* 13:6981-98.
Vieira, J. and Messing, J., *Methods in Enzymology*, 153:3-11 (1987).
Wiederrecht, et al. (1988) *Cell* 54:841.

What is claimed is:

1. A method for enhancing the expression of a plant cell gene having a promoter comprising the upstream sequence motif TGACG, said method comprising inserting into the genome of a plant cell a chimeric gene operatively comprised of a heterologous promoter, a structural gene encoding the ASF-1 protein of FIG. 1, and a 3' nontranslated region joined in a 5' to 3' direction and expressing the ASF-1 protein encoded by said structural gene.

2. A method of claim 1 in which the heterologous promoter is the CaMV35S promoter.

3. A method of claim 1 in which the heterologous promoter is the promoter of the small subunit of ribulose bisphosphate carboxylase gene.

4. A method of claim 1 in which the heterologous promoter is the promoter from the chlorophyll A/B binding protein gene.

5. A method of claim 1 in which the heterologous promoter is a promoter from a heat-shock protein gene.

6. A method of claim 1 in which the heterologous promoter is the promoter from the nopaline synthase gene.

* * * * *